United States Patent [19]

Hurt

[11] 4,008,319

[45] Feb. 15, 1977

[54] O,S-DIALKYL O-BENZOYL-PHENYL PHOSPHOROTHIOLATES AND PHOSPHORODITHIOATES, PESTICIDAL COMPOSITIONS AND METHODS OF USE

[75] Inventor: William S. Hurt, Collegeville, Pa.

[73] Assignee: Rohm and Haas Company, Philadelphia, Pa.

[22] Filed: May 12, 1975

[21] Appl. No.: 576,837

Related U.S. Application Data

[63] Continuation-in-part of Ser. No. 532,128, Dec. 12, 1974, abandoned.

[52] U.S. Cl. .............................. 424/214; 260/940; 260/941; 260/942; 260/943; 260/946; 424/210; 424/211; 424/212
[51] Int. Cl.² ...................... A01N 9/36; C07C 9/18
[58] Field of Search ........... 424/212; 260/940, 941, 260/942, 943, 946; 424/210, 211, 212, 214

[56] References Cited

UNITED STATES PATENTS 3,839,509  10/1974  Drabek et al. ............... 260/946 X
3,839,511  10/1974  Kishimo et al. ............. 260/946 X

*Primary Examiner*—Richard L. Raymond
*Attorney, Agent, or Firm*—George W. F. Simmons; Carl A. Castellan; Betty A. Narducci

[57] ABSTRACT

This invention relates to novel organophosphorothiolates and phosphorodithioates of the formula:

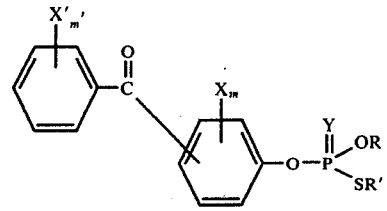

wherein
R is a ($C_1$–$C_4$) alkyl group;
R' is a ($C_3$–$C_6$) alkyl group;
Y is an oxygen atom or a sulfur atom;
X is a halogen atom, a ($C_1$–$C_5$) alkyl group, a ($C_1$–$C_5$) alkoxy group, a trifluoromethyl group, a cyano group, or a group of the formula:

wherein R'' is a hydrogen atom or a ($C_1$–$C_3$) alkyl group;
X' is a halogen atom, a nitro group, a ($C_1$–$C_5$) alkyl group, a ($C_1$–$C_5$) alkoxy group, a trifluoromethyl group, a cyano group, or a group of the formula:

wherein R'' is a hydrogen atom or a ($C_1$–$C_3$) alkyl group; and
m and m' are the same or different and are integers from 0 to 3;

to compositions containing them and to methods of using them to control pests.

19 Claims, No Drawings

O,S-DIALKYL O-BENZOYL-PHENYL PHOSPHOROTHIOLATES AND PHOSPHORODITHIOATES, PESTICIDAL COMPOSITIONS AND METHODS OF USE

This application is a continuation-in-part of U.S. Ser. No. 532,128, filed Dec. 12, 1974, now abandoned.

The present invention relates to novel organophosphorothiolates and phosphorodithioates, having pesticidal activity, especially acaricidal and insecticidal activity, to compositions containing them, and to methods of using them to control various harmful pests. In addition to possessing outstanding pesticidal activity, compounds of the present invention possess a combination of desirable characteristics not possessed by known organophosphorus pesticides. These characteristics include activity against organophosphorus resistant species, residual activity, low toxicity to warm-blooded animals and low phytotoxicity for economically important plant species.

These novel compounds can be represented by the formula:

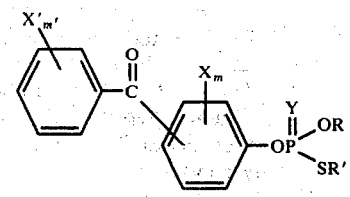
(I)

wherein
R is a $(C_1-C_4)$ alkyl group, preferably methyl or ethyl, most preferably ethyl;
R' is a $(C_3-C_6)$ alkyl group, preferably a $(C_3-C_5)$ alkyl group of the formula:

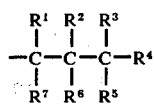

wherein $R^1-R^7$ are individually hydrogen, methyl, or ethyl, preferably hydrogen;
Y is an oxygen atom or a sulfur atom, preferably an oxygen atom,
X is a halogen atom, preferably chlorine; a $(C_1-C_5)$ alkyl group, preferably methyl; a $(C_1-C_5)$ alkoxy group, preferably methoxy; a trifluoromethyl group; a cyano group; or a group of the formula:

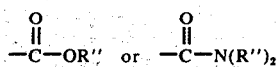

wherein R'' is a hydrogen atom or a $(C_1-C_3)$ alkyl group;
X' is a halogen atom, preferably chlorine; a nitro group; a $(C_1-C_5)$ alkyl group, preferably methyl; a $(C_1-C_5)$ alkoxy group, preferably methoxy; a trifluoromethyl group; a cyano group; or a group of the formula:

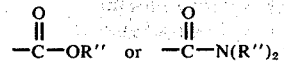

wherein R'' is a hydrogen atom or a $(C_1-C_3)$ alkyl group; and
m and m' are the same or different and are integers from 0 to 3, preferably from 0 to 2.

As used in the specification and claims, the terms "alkyl" and "alkoxy" are intended to include branched chain as well as straight chain alkyl and alkoxy groups. Representative alkyl groups include methyl, ethyl, n-propyl, sec-butyl, isobutyl, n-pentyl, neopentyl, 2-methypentyl, n-hexyl and the like. Representative alkoxy groups include methoxy, ethoxy, propoxy, sec-butoxy, pentoxy and the like.

The organophosphorothiolates and phosphorodithioates described above can exist in their isomeric forms, wherein the benzoyl group of Formula I is attached to the benzene ring in a position which is ortho, meta or para to the point of attachment of the phosphorothiolate or phosphorodithioate group. The preferred compounds of this invention are those in which the benzoyl group is in a position ortho or para to the phosphorothiolate or phosphorodithioate group.

In a preferred embodiment of this invention, the compounds can be represented by the formula:

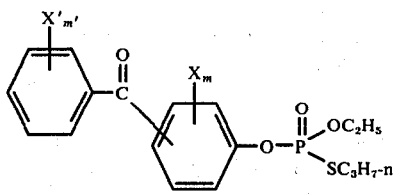
(II)

wherein
X is a $(C_1-C_5)$ alkyl group, preferably methyl; a $(C_1-C_5)$ alkoxy group; preferably methoxy; or a halogen atom, preferably chlorine;
X' is a $(C_1-C_5)$ alkyl group, preferably methyl; or a halogen atom, preferably chlorine;
m is an integer from 0 to 1,
m' is an integer from 0 to 1; and the benzoyl group is in a position ortho or para to the phosphorothiolate group.

Typical compounds within the scope of this invention include:

O-(4-benzoylphenyl) O-methyl S-n-propyl phosphorothiolate

O-(4-benzoylphenyl) O-n-butyl S-n-propyl phosphorothiolate

O-(3-benzoylphenyl) O-ethyl S-n-propyl phosphorothiolate

O-(2-benzoylphenyl) O-ethyl S-isobutyl phosphorothiolate

O-(2-benzoyl-4-chlorophenyl) O-ethyl S-n-propyl phosphorothiolate

O-(2-benzoyl-4-methoxyphenyl) O-ethyl S-n-propyl phosphorothiolate

O-(2-benzoyl-4-isopropylphenyl) O-ethyl S-n-propyl phosphorothiolate

O-[2-(4'-chlorobenzoyl)-4-cyanophenyl] O-ethyl S-isobutyl phosphorothiolate

O-[2-(3'-bromobenzoyl)-4-ethoxyphenyl] O-ethyl S-n-propyl phosphorothiolate

O-[2-(4'-chlorobenzoyl)-4-fluorophenyl] O-ethyl S-isobutyl phosphorothiolate
O-ethyl O-[4-(4'-nitrobenzoyl)phenyl]S-n-propyl phosphorothiolate
O-[4-(4'-cyanobenzoyl)phenyl] O-ethyl S-n-propyl phosphorothiolate
S-sec-butyl O-[4-(4'-dimethylaminocarbonylbenzoyl)-6-bromo-2-chlorophenyl] O-ethyl phosphorothiolate
O-[4-(4'-aminocarbonylbenzoyl)phenyl]S-sec-butyl O-ethyl phosphorothiolate
O-(4-aminocarbonyl-2-benzoylphenyl) O-ethyl S-n-propyl phosphorothiolate
S-n-butyl O-[4-(2-ethoxycarbonylbenzoyl)phenyl] O-ethyl phosphorothiolate
O-[4-(2'-carboxybenzoyl)phenyl] O-methyl S-n-propyl phosphorothiolate
O-[2-(4'-carboxybenzoyl)phenyl] O-ethyl S-isobutyl phosphorothiolate 2
O-ethyl S-isopental O-[4-(3'trifluoromethylbenzoyl)phenyl]phosphorothiolate
S-sec-butyl O-ethyl O-[4-(3,5-bis-trifluoromethylbenzoyl)phenyl]phosphorothiolate
O-(2-benzoyl-5-methylphenyl) O-ethyl S-isobutyl phosphorothiolate
O-(4-benzoyl-2-methylphenyl) O-ethyl S-n-propyl phosphorothiolate
O-[4-(2',4'-dimethylbenzoyl)-2-chlorophenyl] O-ethyl S-n-hexyl phosphorothiolate
O-(4-benzoyl-2,6-dimethylphenyl) O-isopropyl S-n-propyl phosphorothiolate
O-[4-(3', 4'-dichlorobenzoyl)-2-chlorophenyl] O-ethyl S-n-propyl phosphorodithioate
S-sec-butyl O-ethyl O-[4-(2,4,6-trichlorobenzoyl)-phenyl]phosphorodithioate
O-[2-(2', 4'-dichlorobenzoyl-4-chlorophenyl] O-ethyl S-n-propyl phosphorodithioate
O-[4-(4'-cyanobenzoyl)phenyl] O-n-propyl S-n-propyl phosphorodithioate
S-sec-butyl O-[2-(2'-chloro-4'-methylbenzoyl)-4-n-pentylphenyl] O-ethyl phosphorodithioate, and the like.

The compounds of this invention can be prepared by reacting a phenol with an O,S-dialkylphosphorochloridothiolate or phosphorochloridodithioate. The general reaction can be represented by the following equation:

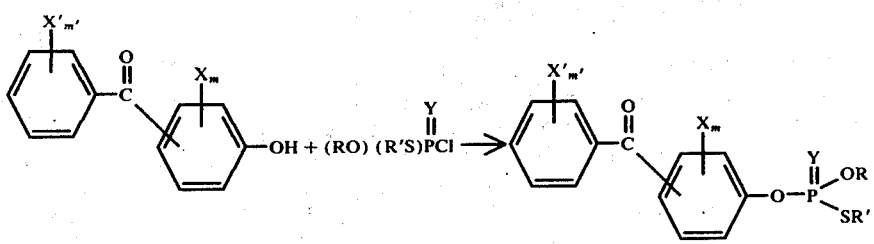

wherein Y, R, R', X, X', m and m' are as defined for Formula I.

An acid acceptor such as a tertiary amine or an alkali carbonate or hydroxide can be employed as a scavenger in the preparation. Representative acid acceptors include pyridine, trimethylamine, triethylamine, dimethylaniline, lithium carbonate, sodium hydroxide, potassium hydroxide and the like. Generally, an equimolar ratio of reactants is preferred but an excess of any of the reactants can be employed. While not required, the reaction is advantageously carried out in the presence of an inert organic solvent such as an aromatic hydrocarbon, halogenated aromatic hydrocarbon, aliphatic hydrocarbon, aliphatic ketone, aliphatic nitrile, ether solvent and the like. Suitable solvents include benzene, toluene, heptane, methylethyl ketone, acetone, ethyl ether, acetonitrile and dioxane. The reaction is generally conducted in a temperature range of about −10° to about 100° C or more, and preferably in the range of about 0° to about 60° C.

In addition to the above procedure, the compounds of this invention can be prepared by reacting an alkali phenoxide with an O,S-dialkylphosphorochloridothiolate or phosphorochloridodithioate. This reaction can be represented by the following equation:

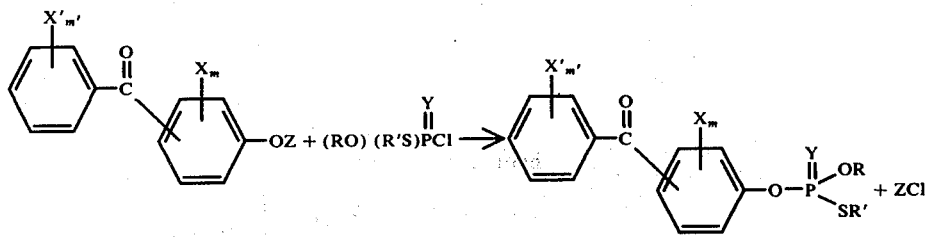

wherein Y, R, R', X, X', m and m'to are as defined for Formula I and Z is an alkali metal, such as sodium, potassium or lithium.

Reaction conditions, including choice of solvents, temperature, and molar ratios correspond to the conditions described above for the reaction with a phenol, except that there is no need to employ an acid acceptor in this reaction.

All of the starting materials used in the preparation of the compounds of this invention are known compounds or are readily prepared by adaptations of known routes. For example, hydroxy benzophenones can be prepared by Friedel-Crafts acylation of substituted phenols as described in detail by P. H. Gore in "Freidal-Crafts and Related Reactions", G. A. Olah, Ed. Vol. 3, Interscience, New York, 1967. The O,S-dialkyl phosphorochloridothiolates are prepared by reacting an alkylsulfenyl chloride with a dialkyl chlorophosphite [A. F. Lippman, J. Org. Chem. 30, 3217 (1965)].

The following examples are given by way of illustration and are not to be considered as limitations of the present invention.

EXAMPLE 1

Preparation of O-(4-benzoylphenyl) O-ethyl S-n-propyl phosphorothiolate

To a solution of 9.9g. (0.05 mole) of 4-hydroxybenzophenone in 150 ml. of anhydrous acetonitrile is added in portions, 2.1g. (0.05 mole) of sodium hydride (57% in mineral oil) at 5° C. The slurry is stirred until no further hydrogen is being evolved. Then, 10.1g. (0.05 mole) of O-ethyl-S-n-propyl phosphorochloridothiolate is added dropwise with stirring over a 30 minute period at 5° C. and allowed to stir overnight at room temperature. The slurry is filtered to remove sodium chloride and the filtrate is concentrated in vacuo to give 16.8g. (91%) of a yellow oil. The oil is taken up in 100 ml. of benzene, washed twice with 50 ml. portions of water, dried over sodium sulfate and reconcentrated in vacuo to give 13.8g. (75%) of the desired product, which is shown by nmr and glc to have a purity of 90%. Further purification by chromatography on silica gel using butyl acetate/heptane as the eluent gives the pure product as a colorless oil.

EXAMPLE 2

Preparation of O-(2-benzoylphenyl) O-ethyl S-n-propyl phosphorothiolate

To a solution of 9.9g. (0.05 mole) of 2-hydroxybenzophenone in 150 ml. of anhydrous acetonitrile is added in portions, 2.1g. (0.05 mole) of sodium hydride (57% in mineral oil) at 5° C. The slurry is stirred until no further hydrogen is evolved. Then, 10.1g. (0.05 mole) of O-ethyl-S-n-propyl phosphorochloridothiolate is added dropwise with stirring over a 30 minute period at 5° C. and allowed to stir overnight at room temperature. The slurry is filtered to remove sodium chloride and the filtrate is concentrated in vacuo to give 13.3g. of a yellow oil. The oil is taken up in 100 ml. of benzene, washed twice with 50 ml. portions of water, dried over sodium sulfate and reconcentrated in vacuo to give 12.8g. (70%) of the desired product, which is shown by nmr and glc to have a purity of 90%. Further purification by chromatography on silica gel using butyl acetate/heptane as the eluent gives the pure product as a pale yellow oil.

EXAMPLE 3

Preparation of O-(2-benzoyl-4-methylphenyl) O-ethyl S-n-propyl phosphorothiolate To a cooled solution of 2.6 g. (0.04 mole) of potassium hydroxide in 100 ml. of methanol under nitrogen is added 8.5 g. (0.04 mole) of 2-hydroxy-5-methyl benzophenone in 20 ml. of methanol. The mixture is concentrated in vacuo at 35°–40° C. and held for 2 days under vacuum to give the potassium phenolate as an orange solid. The phenolate is dissolved in 40 ml. of methyl isobutyl ketone and 8.5 g. (0.042 mole) of O-ethyl S-n-propyl phosphorochloridothiolate is added dropwise to the solution at 25°–50° C. The mixture is heated for 7 hours at 60°–75° and then overnight at 41° C. The slurry is diluted with 100 ml. of benzene, washed once with 140 ml. of a 5:2 mixture of water:isopropanol and once with 250 ml. of a 4:1 mixture of water:isopropanol. The organic layer is dried over sodium sulfate and concentrated in vacuo to give 13.4 g. (89%) of the phosphorothiolate as a yellow oil. The oil is purified by chromatography on silica gel using butyl acetate/heptane as the eluent.

EXAMPLE 8

Preparation of O-ethyl O-[4(4'-methylbenzoyl)phenyl]S-n-propyl phosphorothiolate A solution of 7.4g. (0.035 mole) of 4-hydroxy-4'-methylbenzophenone in 30 ml. of acetonitrile is added in portions to a stirring suspension of 0.85g. (0.035 mole) of sodium hydride in 120 ml of acetonitrile at room temperature. The mixture is stirred until there is no further evolution of hydrogen gas, and then 7.14g. (0.035 mole) of O-ethyl S-n-propyl phosphorochloridothiolate is added dropwise at room temperature.

After stirring for 5 days the reaction is filtered and the filtrate concentrated in vacuo to give 12.2g. (92%) of the desired phosphorothiolate. A portion (4.0g.) is further purified by chromatography on silica gel using butyl acetate/heptane as the eluent to give 1.1g. of the pure product.

EXAMPLE 9

Preparation of O-[4-(benzoyl)phenyl S-sec-butyl O-ethyl phosphorothiolate

A suspension of sodium hydride in 20 ml. of acetonitrile is added to a stirring solution of 4.95 g. (0.025 mole) of 4-hydroxyphenone in 100 ml. of acetonitrile at 5° C. The mixture is stirred for 3 hours at room temperature, and then 5.4 g. (0.025 mole) of S-sec-butyl O-ethyl phosphorochloridothiolate in 10 ml. of acetonitrile is added to the cold (ice bath) sodium salt.

The white suspension is stirred for 2 days at room temperature, filtered to remove sodium chloride and the filtrate concentrated in vacuo. The residue is taken up in 100 ml. of benzene, washed with 100 ml. of water, dried over magnesium sulfate and concentrated in vacuo to give 7.5g. (79%) of the desired phosphorothiolate as a pale yellow liquid.

In a manner similar to the foregoing examples, the following compounds are likewise readily prepared:

O-(2-benzoyl-4-chlorophenyl) O-ethyl S-n-propyl phosphorothiolate

O-(2-benzoyl-5-methoxyphenyl) O-ethyl S-n-propyl phosphorothiolate

O-[2-(4'-chlorobenzoyl)-5-methoxyphenyl] O-ethyl S-n-propyl phosphorothiolate

O-[2-(4'-chlorobenzoyl)-4-fluorophenyl] O-ethyl S-isobutyl phosphorothiolate

O-(3-benzoylphenyl) O-ethyl S-n-propyl phosphorothiolate

O-[3-(4'-cyanobenzoyl)phenyl] O-ethyl S-n-propyl phosphorothiolate

O-[4-(4'-aminocarbonylbenzoyl)phenyl] O-ethyl S-isobutyl phosphorothiolate

S-n-butyl O-[4-(2'-ethoxycarbonylbenzoyl)phenyl] O-ethyl phosphorothiolate

O-ethyl S-isopentyl O-[4-(3'-trifluoromethylbenzoyl)phenyl] phosphorothiolate

O-(4-benzoyl-2-methylphenyl) O-ethyl S-n-propyl phosphorothiolate

O-[2-(2',4'-dichlorobenzoyl)-4-chlorophenyl] O-ethyl S-n-propyl phosphorodithioate

TABLE I

ELEMENTAL ANALYSIS $$\text{Z} \underset{}{\overset{X}{\bigotimes}} - O - \overset{O}{\underset{SR'}{\overset{\|}{P}}} - OC_2H_5$$

| Ex. No. | Z | X | R' | C | H | P | S |
|---|---|---|---|---|---|---|---|
| 1 | 4-($\phi\overset{O}{\overset{\|}{C}}-$) | H | $C_3H_7n$ | 59.3 (59.2) | 5.81 (6.06) | 8.50 (8.54) | — |
| 2 | 2-($\phi\overset{O}{\overset{\|}{C}}-$) | H | $C_3H_7n$ | 59.3 (59.5) | 5.81 (5.53) | 8.50 (7.87) | — |
| 3 | 2-($\phi\overset{O}{\overset{\|}{C}}-$) | 4-$CH_3$ | $C_3H_7n$ | 60.3 (60.0) | 6.13 (6.01) | 8.19 (8.37) | 8.47 (8.45) |
| 4 | 2-($\phi\overset{O}{\overset{\|}{C}}-$) | 4-Cl | $C_3H_7n$ | 54.2 (54.3) | 5.05 (5.24) | 7.77 (7.60) | 8.04 (8.50) |
| 5 | 3-($\phi\overset{O}{\overset{\|}{C}}-$) | H | $C_3H_7n$ | 59.3 (59.5) | 5.81 (5.98) | 8.50 (8.24) | — |
| 6 | 2-($\phi\overset{O}{\overset{\|}{C}}-$) | 5-$OCH_3$ | $C_3H_7n$ | 57.9 (58.3) | 5.88 (5.98) | 7.85 (7.35) | — |
| 7 | 2-(4'-Cl$\phi\overset{O}{\overset{\|}{C}}-$) | 5-$OCH_3$ | $C_3H_7n$ | 53.2 (53.5) | 5.17 (5.45) | 7.22 (6.72) | 8.27 (8.08) |
| 8 | 4-(4'-$CH_3\phi-\overset{O}{\overset{\|}{C}}-$) | H | $C_3H_7n$ | 60.3 (59.6) | 6.13 (6.46) | 8.18 (8.20) | — |
| 9 | 4-($\phi\overset{O}{\overset{\|}{C}}-$) | H | $C_4H_9$sec | 60.3 (60.3) | 6.13 (6.49) | 8.19 (7.37) | — |

The organophosphorothiolates and phosphorodithioates of this invention possess general utility as arthropodicides, particularly against members of the class Arachnoidea, which includes the order Acarina, as represented by mites and ticks, and Insecta, the insects. Certain compounds of this invention are also active as nematocides, ovicides, larvicides, and fungicides, particularly phytopathogenic fungicides.

Initial evaluations are made on the following mite, insects and nematode:

| Code Symbol | Common Name | Latin Name |
|---|---|---|
| TSM | Two-spotted spider mite | Tetranychus urticae |
| GPA | Green peach aphid | Myzus persicae |
| BB | Mexican bean beetle | Epilachna varivestis |
| AW | Southern armyworm | Spodoptera eridania |
| BW | Boll weevil | Anthonomus grandis |
| LST | Lone star tick | Amblyoma americanum |
| HF | House fly | Musca domestica |
| SF | Stable fly | Stomoxys calcitrans |
| Nema | Southern root knot nematode | Meloidogyne incognita |

A test solution containing 600 ppm of test compound can be made by dissolving the test compound in a solvent (acetone:methanol, 1:1), adding surfactant and then water to give an acetone:methanol:water system of 10:10:80. A 1:1 mixture of an alkylarylpolyetheralcohol (commercially available under the trademark Triton X-155) and a modified phthalic glycerol alkyd resin (commercially available under the trademark Triton B-1956) can be utilized at the equivalent of one ounce per gallon of test solution as a surfactant.

For the mite test, infested bean (*phaseolus limeanus*) leaf discs (1.25 inches in diameter) containing about 50 mites and for green peach aphid tests, infested broccoli (*Brassica oleracea italica*) leaves or portions thereof containing about 50 aphids are placed in a Petri dish lid on a moistened piece of cotton. The leaves are then sprayed with the test solution using a rotating turntable. They are held for 24 hours and then the percent kill is determined.

For the bean beetle and armyworm test, detached bean leaves on pieces of moistened filter paper are sprayed as above for the mite test in similar dishes and allowed to dry. One such dish is infested with 10 third instar Mexican bean beetle larvae, while another is infested with 10 third instar southern armyworm larvae. The dishes are covered. After holding for 48 hours, the percent kill is obtained.

For the boll weevil and house fly tests, half pint glass canning jars with a screened top are used. Food is supplied for the boll weevil (apple) and for the house fly (sugar water). The test insects consist of 10 adult boll weevils and 20 adult house flies. The jars containing the insects are sprayed using the turntable. The percent kill of boll weevil is determined 48 hours after the application. In the house fly test, a percent knockdown is determined one hour after application, the percent kill after 24 hours.

For the tick test, plastic Petri dish bottoms containing a piece of filter paper are sprayed with the test compounds. After the filter paper dries, a small quantity of water is pipetted into each dish to insure proper humidity. The dishes are then infested with about 50 lone star tick larvae and capped with tight-fitting plastic lids. After holding for 24 hours, the percent kill is obtained.

For the stable fly test, glass Mason half-pint jars with a piece of filter paper covering the bottom of each jar, are infested with 20, 3–5 day old male and female stable flies. Screening, held in place with screw-cap lids, is used to confine the flies. The jars containing the flies are sprayed directly on a turntable sprayer. The flies are held at 80° F. and 55% relative humidity for a 1 hour knock-down (KD) and 24-hour mortality observation. Results are recorded as the number of flies knocked down or dead per total number.

For the nematode test, soil is homogeneously inoculated with a macerated blend of tomato roots heavily knotted with the root knot nematode. Ten milliliters of the test solution are added to 200 milliliters of the inoculated soil in a 16 oz. jar to give a concentration by volume of about 30 ppm. The jar is then shaken to insure thorough mixing, immediately uncapped, and allowed to air for 24 hours. The soil is then placed into a 3 inch plastic pot after which time 3 cucumber (Cucumis sativus) seeds are planted. About 23 days thereafter, the cucumber plants are removed from the soil and the root system examined for the presence of knots. A total of 25 knots or less is considered as a measure of control.

Table II gives the results of the foregoing biological evaluations.

eggs in about one milliliter of water are pipetted onto the filter paper and the dishes covered. These are held for 6 days and examined under the microscope. The percent kill values for ova and larvae are determined.

For the mosquito larvae test, approximately 20, 3-day old yellow fever mosquito larvae (Aedes aegypti) are introduced into styrofoam cups containing 100 ml. of water which has previously been treated with a test solution of selected compounds so as to give a 1 ppm concentration. Twenty-four hours later, the percent kill is determined.

Table III gives the results of these ovicidal and larvicidal tests.

TABLE III

OVICIDAL AND LARVICIDAL EVALUATIONS
Percent Kill

| EX. NO. | Corn Rootworm at 600 ppm | | Two Spotted Mite at 150 ppm | | Mosquito Larvae 1 ppm |
|---|---|---|---|---|---|
| | O | L | O | L | |
| 1 | 92 | 100 | 49 | 100 | 100 |
| 2 | 41<sup>a</sup> | 100<sup>a</sup> | 94 | 100 | 100 |
| 3 | 0<sup>a</sup> | 100<sup>a</sup> | 81 | 100 | 100 |
| 4 | 0 | 100 | 89 | 100 | 100 |
| 5 | 84 | 100 | 0 | 100 | 100 |
| 6 | 0 | 100 | 0 | 72 | 100 |
| 7 | 0 | 100 | 0 | 100 | 100 |
| 8 | 0 | 95 | 0 | 0 | 100 |
| 9 | 59 | 93 | NT | NT | 100 |

NT = Not tested
<sup>a</sup>=percent control at 150 ppm.

Fungicidal evaluation of compounds of this invention is carried out by way of a foliar screening test. The general procedure for the fungicidal test is to take potted plants in proper condition of growth for susceptibility to the plant diseases to be evaluated, to spray

TABLE II

ACARICIDAL, INSECTICIDAL, and NEMATOCIDAL DATA
Percent Control, etc. at 600 ppm.

| Ex. No. | TSM | GPA | BB | AW | BW | LST | HF KD | HF KILLED | SF KD | SF KILLED | Nema<sup>b</sup> |
|---|---|---|---|---|---|---|---|---|---|---|---|
| 1 | 100 | 100 | 100 | 100 | 40 | 100 | 100 | 100 | 100 | 100 | — |
| 2 | 100 | 100 | 100 | 100 | 80 | 100 | 95 | 100 | 100 | 100 | + |
| 3 | 100 | 100 | 100 | 100 | 100 | 0 | 95 | 100 | 70 | 75 | — |
| 4 | 100 | 100 | 100 | 100 | 100 | 0 | 55 | 75 | 0 | 90 | + |
| 5 | 100 | 100 | 100 | 100 | 20 | 100 | 100 | 100 | 95 | 100 | + |
| 6 | 100 | 100 | 100 | 100 | 40 | 100 | 95 | 100 | 30 | 80 | + |
| 7 | 100 | 100 | 100 | 100 | 80 | 100 | 80 | 100 | 0 | 30 | + |
| 8 | 100 | 100 | 100 | 100 | 80 | 0 | 100 | 100 | 100 | 100 | + |
| 9 | 100 | 100 | 100 | 100<sup>a</sup> | 100 | 0 | 100 | 100 | 100 | 100 | + |

<sup>a</sup>=Percent control at 150 ppm.
<sup>b</sup>= + means control — means no control
KD=Knockdown Ovicidal and larvicidal tests are conducted on representative compounds of this invention. These compounds demonstrate ovicidal and larvicidal activity.

For mite tests involving the two-spotted mite ova and larvae, bean leaf sections containing about 100 eggs are placed on moistened cotton in a Petri dish and sprayed on the turntable with a 150 ppm test solution. These are held for 6 days and examined under the microscope. Unhatched eggs and dead and live larvae are counted and the percent ovicidal and larvicidal activity are determined.

For tests involving the southern corn rootworm (Diabrotica undecimpunctata howardi) ova and larvae, two layers of 4.25 cm. filter papers are placed in small, Petri dishes, and sprayed on the turntable with a 600 ppm solution of the test compound and air dried. About 100 these on a moving belt and allow them to dry. The plants are then inoculated with the respective fungal spores and allowed to incubate until the disease symptoms and the disease control are read or estimated. Percentage of disease control is recorded.

Compounds of the present invention are tested at a concentration of 300 ppm in a solution or suspension made by dissolving a weighed amount of the candidate fungicide in a 50:50 mixture of acetone and methanol and then adding an equal volume of water.

Some of the plant diseases controlled by compounds of this invention include the following:

| Code Symbol | Common Name | Latin Name |
|---|---|---|
| GDM | Grape Downy Mildew | Plasmopara viticola |
| RB | Rice Blast | Piricularia oryzae |

-continued

| Code Symbol | Common Name | Latin Name |
|---|---|---|
| TLB | Tomato Late Blight | Phytophthora infestans |
| WLR | Wheat Leaf Rust | Puccinia recordita |

Table IV gives the results of the foregoing fungicidal evaluations.

TABLE IV

FUNGICIDAL DATA
Percent Kill at 300 ppm

| Ex. No. | GDM | RB | TLB | WLR |
|---|---|---|---|---|
| 1 | E | E | E | A |
| 2 | E | E | E | E |
| 3 | B | E | B | E |
| 4 | B | A | E | A |

The compounds of the present invention are used for protection of plants and animals, including man, from the ravages of harmful and annoying pests or disease organisms which they may carry. The term "pest" as used herein is intended to include arthropods, such as insects and acarids in all stages of development, nematodes, fungi, such as phytopathogenic fungi, and the like. Generally, control of a living organism is achieved in accordance with this invention by application of the compounds in pesticidally effective amounts either directly to the pests to be controlled or to the loci to be freed of or protected from attack by such pests. For example, food, fiber, forage, forest, and ornamental crops and stored products thereof would represent plant protection loci. Treatment with compounds of this invention of domestic animals, man and their immediate environs similarly constitute representative loci for protection against various annoying ectoparasitic or endoparasitic Acarina (Acari) and Insecta. Accordingly, compounds of the present invention provide utility as the essential active ingredient of pesticidal compositions suitable for agricultural and sanitary purposes.

The term "control" as employed in the specification and claims of this application is to be construed as any means which adversely affects the existence or growth of a living organism. Such means can comprise a complete killing action, eradication, arresting in growth, inhibition, reduction in number or any combination thereof.

For use as pesticides the compounds of this invention can be used as solutions in organic solvents or formulations. For example, they can be formulated as wettable powders, emulsifiable concentrates, dusts, granular formulations or flowable emulsifiable concentrates. In such formulations, the organophosphorothiolates or phosphorodithioates are extended with an agronomically acceptable liquid or solid carrier and, when desired, suitable surfactants are likewise incorporated. Surfactants commonly used in the art can be found in the John W. McCutcheon, Inc. publication "Detergents and Emulsifiers Annual".

The organophosphorothiolate or phosphorodithioate can be taken up on or mixed with a finely particled solid carrier, as for example, clays, inorganic silicates, carbonates, and silicas. Organic carriers can also be employed. Dust concentrates are commonly made wherein organophosphorothiolates or phosphorodithioates are present in the range of about 20 to about 80%. For ultimate applications, these concentrates are normally extended with additional solid to give an active ingredient content of from about 1 to about 20%. Granular formulations are made using a granular or pelletized form of carrier, such as granular clays, vermiculite, charcoal or corn cobs, and can contain the active ingredient in from about 1 to about 25% by weight.

Wettable powder formulations are made by incorporating the compounds of this invention in an inert, finely divided solid carrier along with a surfactant which can be one or more emulsifying, wetting, dispersing or spreading agents or blend of these. The organophosphorothiolates or phosphorodithioates are usually present in the range of about 10 to about 80% by weight and surfactants form about 0.5 to about 10% by weight.

One convenient method for preparing a solid formulation is to impregnate the organophosphorothiolate or phosphorodithioate onto the solid carrier by means of a volatile solvent such as acetone. In this manner, adjuvants, such as activators, adhesives, plant nutrients, synergists and various surfactants can also be incorporated.

Emulsifiable concentrate formulations can be prepared by dissolving organophosphorothiolates or phosphorodithioates of this invention in an agronomically acceptable organic solvent and adding a solvent-soluble emulsifying agent. Suitable solvents are usually water-immiscible and can be found in the hydrocarbon, ketone, ester, alcohol and amide groups of organic solvents. Mixtures of solvents are commonly employed. The surfactants useful as emulsifying agents can constitute about 0.5 to about 10% by weight of emulsifiable concentrate and can be anionic, cationic or non-ionic in character. The concentration of the active ingredients can vary from about 10 to about 80%, preferably in the range of about 25 to about 50%.

For use as pesticidal agents, these compounds should be applied in an effective amount sufficient to exert the desired pesticidal activity by techniques well known in the art. Usually, this will involve the application of the organophosphorothiolate or phosphorodithioate to the loci to be protected from or freed of pests in an effective amount when incorporated in an agronomically acceptable carrier. However, in certain situations, it may be desirable and advantageous to apply the compounds directly onto the loci to be protected from or freed of pests without the benefit of any substantial amount of carrier. This is a particularly effective method when the physical nature of the toxicants is such as to permit what is known as "low-volume" application, that is, when the compounds are in liquid form on substantially soluble in higher boiling solvents.

The application rate will, of course, vary depending upon the purposes for such application, the organophosphorothiolates or phosphorodithioates being utilized, the frequency of dissemination and the like.

By "agronomically acceptable carrier" is meant any substance which can be utilized to dissolve, disperse or diffuse the chemical incorporated therein without impairing the effectiveness of the toxic agent and which does no permanent damage to such environment as soil, equipment and agronomic crops.

Many of the above formulations can be utilized on animals for control of parasites.

For use as insecticides and acaricides, dilute sprays can be applied at concentrations of about 0.001 to about 20 pounds of the active organophosphorothiolate or phosphorodithioate ingredient per 100 gallons of spray. They are usually applied at about 0.01 to about 5 pounds per 100 gallons. In more concentrated sprays, the active ingredient is increased by a factor of about 2 to about 12. With dilute sprays, applications are usually made to the plants until run off is achieved, whereas with more concentrated low-volume sprays, the materials are applied as mists.

For use as a nematocide or as a soil insecticide, the organophosphorothiolates or phosphorodithioates can be applied as a solid formulation, preferably a granular formulation, by broadcasting, side-dressing, soil incorporation or seed treatment. The application rate can be from about 1 to about 50 pounds per acre. For soil incorporation, the compounds of this invention can be mixed with the soil at a rate of about 2 to about 100 ppm.

For use as a fungicide, the organophosphorothiolates or phosphorodithioates can be applied as fungicidal sprays by methods commonly employed, such as conventional high-gallonage hydraulic sprays, low-gallonage sprays, air-blast sprays, aerial sprays and dusts. The dilution and rate of application will depend upon the type of equipment employed, the method of application and diseases to be controlled, but the preferred effective amount is usually about 0.1 lb. to 50 lbs. per acre of the active ingredient. As a fungicidal seed protectant, the amount of toxicant coated on the seed is usually at a dosage rate of about 0.1 to 20 ounces per hundred pounds of seed. As a soil fungicide the chemical can be incorporated in the soil or applied to the surface usually at a rate of 0.1 to 50 lbs. per acre. As a foliar fungicide, the toxicant is usually applied to growing plants at a rate of 0.25 to 10 lbs. per acre.

The compounds of this invention can be utilized as the sole pesticidal agents or they can be employed in conjunction with other bactericides, fungicides, herbicides, insecticides, acaricides, nematocides and comparable pesticides.

Many variations of this invention are possible without departing from the spirit or scope thereof.

We claim:

1. A compound of the formula:

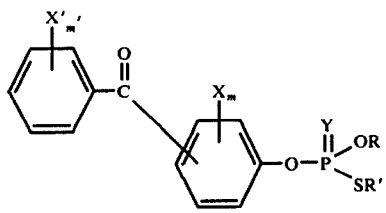

wherein
R is a $(C_1-C_4)$ alkyl group;
R' is a $(C_3-C_6)$ alkyl group;
Y is an oxygen atom or a sulfur atom;
X is a halogen atom, a $(C_1-C_5)$ alkyl group, a $(C_1-C_5)$ alkoxy group, a trifluoromethyl group, a cyano group, or a group of the formula:

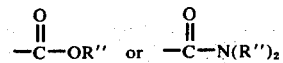

wherein R'' is a hydrogen atom or a $(C_1-C_3)$ alkyl group;
X' is a halogen atom, a nitro group, a $(C_1-C_5)$ alkyl group, a $(C_1-C_5)$ alkoxy group, a trifluoromethyl group, a cyano group, or a group of the formula:

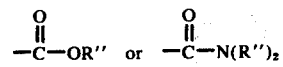

wherein R'' is a hydrogen atom or a $(C_1-C_3)$ alkyl group; and
m and m' are the same or different, and are integers from 0 to 3.

2. A compound according to claim 1 wherein R' is a $(C_3-C_5)$ alkyl group of the formula:

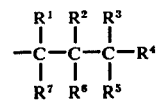

wherein $R^1$–$R^7$ are individually hydrogen, methyl or ethyl.

3. A compound according to claim 2 wherein R is an ethyl group.

4. A compound according to claim 3 wherein Y is an oxygen atom.

5. A compound according to claim 4 wherein the benzoyl group is ortho or para to the phosphorothiolate group.

6. A compound according to claim 5 wherein
X is a $(C_1-C_5)$ alkyl group; a $(C_1-C_5)$ alkoxy group; or a halogen atom;
X' is a $(C_1-C_5)$ alkyl group, or a halogen atom;
m is an integer from 0 to 1, and
m' is an integer from 0 to 1.

7. A compound according to claim 6 wherein
X is a methyl group, a methoxy group or a chlorine atom; and
X' is a methyl group or a chlorine atom.

8. A compound according to claim 6 having the formula:

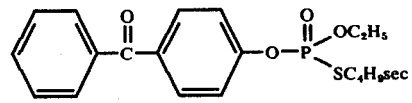

9. A compound according to claim 6 wherein R' is a n-propyl group.

10. A compound according to claim 9 having the formula:

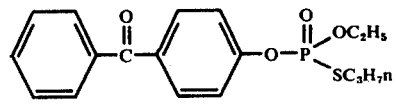

11. A compound according to claim 9 having the formula:

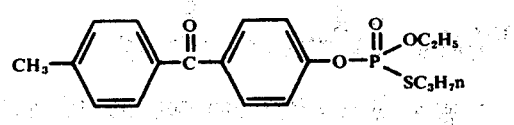

12. A compound according to claim 9 having the formula

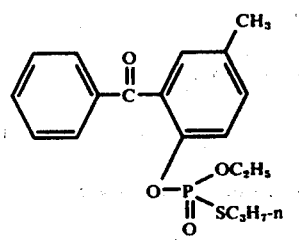

13. A pesticidal composition comprising a pesticidally effective amount of a compound according to claim 1 and an agronomically acceptable carrier.

14. A pesticidal composition comprising a pesticidally effective amount of a compound according to claim 6 and an agronomically acceptable carrier.

15. A method of controlling pests which comprises applying directly to the pests or to the loci to be freed of or protected from attack by such pests, a pesticidally effective amount of the compound of claim 1.

16. A method of controlling pests which comprises applying directly to the pests or to the loci to be freed of or protected from attack by such pests, a pesticidally effective amount of the composition of claim 13.

17. A method according to claim 16 wherein the pests are acarids or insects.

18. A method according to claim 16 wherein the pests are nematodes.

19. A method according to claim 16 wherein the pests are phytopathogenic fungi.

* * * * *